United States Patent
Liu et al.

(10) Patent No.: US 10,806,383 B2
(45) Date of Patent: Oct. 20, 2020

(54) IMPLANTABLE DISSOLVED OXYGEN SENSOR AND METHODS OF USE

(75) Inventors: Vincent Hok Liu, Cambridge, MA (US); Christophoros Christou Vassiliou, Cambridge, MA (US); Yibo Ling, Cambridge, MA (US); Michael J. Cima, Winchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1074 days.

(21) Appl. No.: 13/643,707

(22) PCT Filed: May 4, 2011

(86) PCT No.: PCT/US2011/035146
§ 371 (c)(1),
(2), (4) Date: Oct. 26, 2012

(87) PCT Pub. No.: WO2011/140193
PCT Pub. Date: Nov. 10, 2011

(65) Prior Publication Data
US 2013/0046164 A1    Feb. 21, 2013

Related U.S. Application Data

(60) Provisional application No. 61/331,236, filed on May 4, 2010.

(51) Int. Cl.
*A61B 5/145*   (2006.01)
*A61B 5/00*   (2006.01)
(Continued)

(52) U.S. Cl.
CPC .......... *A61B 5/14503* (2013.01); *A61B 5/415* (2013.01); *A61B 5/418* (2013.01);
(Continued)

(58) Field of Classification Search
CPC ....... A61B 19/54; A61K 49/18; A61K 49/223
See application file for complete search history.

(56) References Cited

U.S. PATENT DOCUMENTS 5,233,991 A    8/1993   Wright
5,258,313 A    11/1993  Moussavi
(Continued)

FOREIGN PATENT DOCUMENTS

WO         94/03210 A1      2/1994
WO         2005/097208 A2   10/2005

OTHER PUBLICATIONS

Kodibagkar VD, Wang X, Pacheco-Torres J, Gulaka P, Mason RP. Proton imaging of siloxanes to map tissue oxygenation levels (PISTOL): a tool for quantitative tissue oximetry. NMR in biomedicine. 2008;21(8):899-907. doi:10.1002/nbm.1279.*

(Continued)

*Primary Examiner* — Etsub D Berhanu
*Assistant Examiner* — Michael A Catina
(74) *Attorney, Agent, or Firm* — Eversheds Sutherland (US) LLP

(57) ABSTRACT

A sensor is provided for measuring a dissolved oxygen concentration in vivo when implanted at a tissue site and in ex vivo applications. The sensor includes an article comprising a sensing medium retained within the implantable article by an oxygen-permeable material. The sensing medium comprises an MR contrast agent for oxygen. The sensor is configured to indicate the dissolved oxygen concentration of a fluid, e.g., in vivo at the tissue site, when subjected to an MR-based method.

9 Claims, 7 Drawing Sheets

(51) Int. Cl.
*G01R 33/56* (2006.01)
*A61K 49/10* (2006.01)
*A61B 5/055* (2006.01)
*G01R 33/44* (2006.01)

(52) U.S. Cl.
CPC .......... *A61K 49/10* (2013.01); *G01R 33/5601* (2013.01); *A61B 5/055* (2013.01); *G01R 33/448* (2013.01)

(56) References Cited

U.S. PATENT DOCUMENTS

| | | | |
|---|---|---|---|
| 5,494,030 A | 2/1996 | Swartz et al. | |
| 5,498,421 A * | 3/1996 | Grinstaff | A23L 1/296 424/450 |
| 5,527,521 A | 6/1996 | Unger | |
| 5,706,805 A | 1/1998 | Swartz et al. | |
| 5,765,562 A | 6/1998 | Leunbach et al. | |
| 5,833,601 A | 11/1998 | Swartz et al. | |
| 6,256,522 B1 * | 7/2001 | Schultz | A61B 5/14532 600/310 |
| 6,256,527 B1 | 7/2001 | Leunbach et al. | |
| 6,589,506 B2 * | 7/2003 | Cremillieux | G01R 33/5601 424/9.3 |
| 6,901,281 B2 | 5/2005 | Bjornerud et al. | |
| 7,097,825 B2 | 8/2006 | Gerber | |
| 7,662,362 B2 | 2/2010 | Kuppusamy et al. | |
| 2003/0199687 A1 * | 10/2003 | Yalpani | C08B 11/06 536/56 |
| 2006/0177379 A1 * | 8/2006 | Asgari | A61K 47/48992 424/9.3 |
| 2007/0135698 A1 * | 6/2007 | Shah | C12Q 1/006 600/348 |
| 2010/0239679 A1 * | 9/2010 | Greene | A01N 25/26 424/490 |
| 2010/0287887 A1 * | 11/2010 | Bolan | G01R 33/5601 53/452 |
| 2011/0288234 A1 * | 11/2011 | Pandey | A61K 49/0032 525/54.1 |

OTHER PUBLICATIONS

Noth et al., "F-MRI in vivo Determination of the Partial Oxygen Pressure in Perfluorocarbon-Loaded Alginate Capsules Implanted into the Peritoneal Cavity and Different Tissues," Magnetic Resonance in Medicine, 1999, p. 1039-1047; vol. 42.

PCT International Search Report for PCT/US2011/035146 dated Aug. 19, 2011 (5 pages).

Kodibagkar et al., "Novel 1H NMR Approach to Quantitative Tissue Oximetry Using Hexamethyldisiloxane," Magnetic Resonance in Medicine, 2006, 55:743-748.

* cited by examiner

IMPLANTABLE DISSOLVED OXYGEN SENSOR AND METHODS OF USE

REFERENCES TO RELATED APPLICATIONS

This application is a national phase entry of PCT Patent Application No. PCT/US2011/035146, filed on May 4, 2011, designating the United States of America, and claims priority to U.S. Provisional Application No. 61/331,236, filed on May 4, 2010, which is incorporated by reference herein in its entirety.

STATEMENT REGARDING FEDERALLY SPONSORED RESEARCH OR DEVELOPMENT

This invention as made with government support under Grant No. U54 CA119349 awarded by the National Institutes of Health. The government has certain rights in the invention.

BACKGROUND

The present invention is generally in the field of sensor devices. More particularly, the present invention relates to a sensor device that may be used to detect or measure the presence of oxygen in a fluid, such as a gas or liquid.

The concentration of dissolved oxygen within biological fluids may provide important information about biological systems. As an essential nutrient and metabolite, the concentration of dissolved oxygen in microenvironments is influenced by a number of factors, such as cellular activity, and can possibly be used to evaluate disease states. It is well known, for example, that the hypoxic state of a tumor negatively affects the efficacy of non-surgical therapies, especially with radiotherapy. Strategies to mitigate hypoxia in tumors before therapy are thought to result in improved outcomes for patients. Real-time knowledge of intratumoral dissolved oxygen would allow a physician to schedule therapy at the most opportune moment to improve outcome. Dissolved oxygen can, for example, be used to estimate the required dose of radiation or the appropriate regimen of chemotherapy. In addition, dissolved oxygen measurements can be used to assess the stage of compartment syndrome in trauma patients.

Current standard methods to measure intratumoral dissolved oxygen in patients are invasive, as they rely on probes directly linked to the measuring instruments. These instruments are not suited for repeated measurements or measurement of non-superficial tumors. The current standard for hypoxia measurement in tumors is $pO_2$ histography. This technique uses a polarographic needle electrode to obtain an Eppendorf histograph, a frequency distribution of oxygen partial pressures measured at several points along a tumor. The needle is guided by computed tomography fluoroscopy to allow physicians to visualize its location in real time. This technique is limited to superficial tumors or metastatic lymph nodes because of the invasiveness of the needle, and results in significant patient discomfort. A number of non-invasive methods have been developed to circumvent the limitations of $pO_2$ histography, based on electron paramagnetic resonance (EPR) oximetry, positron emission tomography (PET), single photon emission computed tomography (SPECT) and MRI. However, improved methods are needed. For example, some of these methods rely on the administration of a contrast agent. The distribution of the contrast agent within the tumor is not precisely known which limits the ability to interpret the results.

It therefore would be desirable to provide a sensor that provides the ability to take repeated measurements at the same location over extended periods. This can be particularly valuable where continual monitoring of in vivo dissolved oxygen levels is required or beneficial.

SUMMARY

In one aspect, a sensor is provided for measuring a dissolved oxygen concentration in vivo when implanted at a tissue site. The sensor comprises an implantable article comprising a sensing medium retained within the implantable article by an oxygen-permeable material. The sensing medium comprises an MR contrast agent for oxygen. The sensor is configured to indicate the dissolved oxygen concentration in vivo at the tissue site when subjected to an MR-based method. In one embodiment, an implantable sensor includes a container having a reservoir and a reservoir opening; an oxygen-permeable membrane covering the reservoir opening; and a sensing medium contained in the reservoir, the sensing medium comprising an MR contrast agent for oxygen. The sensor is configured to indicate the dissolved oxygen concentration of the fluid when subjected to an MR-based method. In another embodiment, the implantable sensor includes one or more beads or microspheres which comprise an agent having an MR relaxivity that is sensitive to oxygen. The one or more beads or microspheres may be injectable, for example in a fluid suspending media, and possess a volume of the agent effective to indicate the dissolved oxygen concentration of the tissue site in vivo when subjected to an MR-based method.

In another aspect, a method is provided for measuring a dissolved oxygen concentration in vivo of a tissue site of a patient. The method includes deploying a sensor at the tissue site in the patient, the sensor comprising a sensing medium, the sensing medium comprising an MR contrast agent for oxygen; and thereafter subjecting the tissue site to electromagnetic radiation and employing an MR-based spectroscopy or other method to analyze the dissolved oxygen concentration in vivo at the tissue site.

In yet another aspect, uses for a dissolved oxygen sensor are provided. For example, the sensor may be used to evaluate the state of a tumor, to determine the presence of hypoxia, to evaluate the effectiveness of a treatment strategy on a patient, to schedule therapies at an opportune time to achieve an improved patient outcome, to monitor metabolic activities in specific regions or organs of the body.

In still another aspect, sensor devices and methods for ex vivo applications are provided for measuring oxygen concentration. The method may include placing a sensor at a location, e.g., in a process stream, in which the sensor is exposed to a fluid to be analyzed, the sensor comprising a sensing medium, the sensing medium comprising an MR contrast agent for oxygen; and thereafter subjecting the sensor to electromagnetic radiation and analyzing the dissolved oxygen concentration by measuring a change in relaxivity of the sensing medium while the sensor is exposed to the fluid to be analyzed.

DETAILED DESCRIPTION

Figure 1:
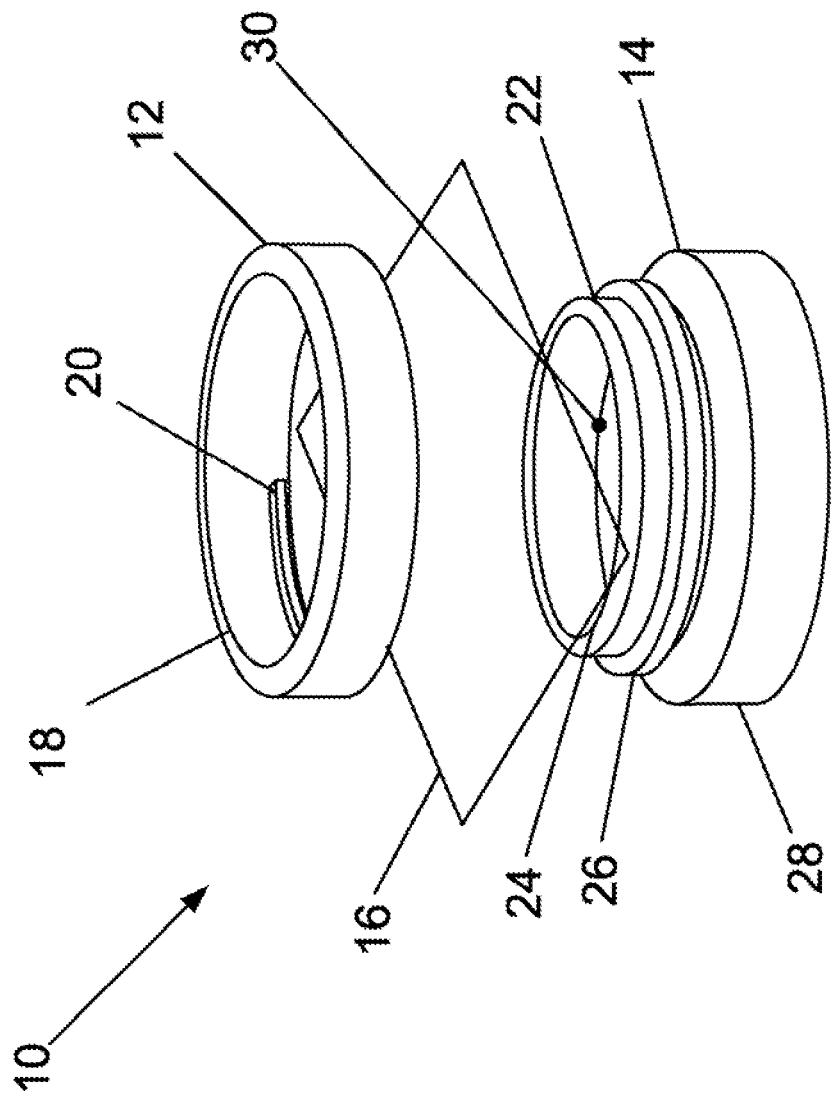
FIG. 1 is an exploded perspective view, illustrating an embodiment of a sensor having a reservoir for containing an MR contrast agent for oxygen.

In one aspect, an implantable sensor is provided for measuring the dissolved oxygen concentration of a fluid in vivo. The implantable sensor may be wholly deployable and implantable within a patient and may include a sensing material that is a magnetic resonance (MR) contrast agent for oxygen. The term "implantable" as used herein refers to a device that is configured for implantation. That is, the device is to be introduced into a subject's body by a surgical or medical procedure and remain there after the procedure. The term "wholly deployable" or "wholly deployed" and "wholly implanted" or "wholly implantable" means that there is not a portion of the sensor device that extends out of the patient transcutaneously or from an anatomical orifice. For example, the device may be sized and shaped to be wholly deployed in the body of a human or animal and to remain deployed for a period of time, such as 30 days or more. The device also may have suitable sterility, biocompatibility, and physical and/or chemical integrity to be implanted and remain implanted over the intended duration of use of the device.

Advantageously, in some embodiments, the sensor may be wholly deployed in vivo and subjected to repeated measurements thereby overcoming the problems associated with repetitive invasive measurement procedures. Moreover, in some embodiments, the sensor may be wholly deployed to a specific target tissue site of interest to allow for site-specific measurement and analysis. Furthermore, the sensor, which comprises an MR contrast agent for oxygen, may provide a higher degree of measurement sensitivity, accuracy, and precision with respect to oxygen concentration than other measurement techniques. The sensor may be employed in various patients or subjects including human or other mammals.

In one embodiment, the implantable sensor may include a container having a reservoir and a reservoir opening, an oxygen-permeable membrane covering the reservoir opening, and a sensing medium contained in the reservoir. The sensing medium may comprise a MR contrast agent for oxygen, and the sensor may be configured to indicate the dissolved oxygen concentration of the fluid when subjected to MR-based methods. In another embodiment, the implantable sensor may comprise a solid polymeric article that has an MR contrast agent for oxygen integrated with the polymeric structure of the article. In certain embodiments, the implantable sensor may be in the form of beads or microspheres which have an MR contrast agent for oxygen incorporated within the bead or microsphere.

In another aspect, a method is provided for measuring a dissolved oxygen concentration of a fluid in vivo. The method may include deploying a sensor at a tissue site, and thereafter subjecting the tissue site to electromagnetic radiation and employing MR-based methods to analyze the dissolved oxygen concentration of the fluid. The sensor may comprise a sensing medium that comprises an MR contrast agent for oxygen. The MR contrast agent may be contained in a reservoir provided with the sensor. Sensing media is prevented from escaping the device with the use of an impermeable membrane (impermeable to the sensing media, but permeable to dissolved oxygen).

In other aspects, sensors and methods are provided for measuring oxygen concentrations in ex vivo environments. Such sensors and methods may utilize the direct measurement of the NMR relaxivity of a sensing medium in contact with the liquid or gas of interest. The oxygen sensors may have advantages over conventional oxygen sensors that are based on a surface reaction such as the automotive oxygen sensor which requires oxygen to react at a precious metal electrode in contact with a solid electrolyte. The present sensors may absorb oxygen throughout the bulk of the material and may therefore be less sensitive to contamination.

Sensors

Implantable sensors are provided for measuring the dissolved oxygen concentration of a fluid in vivo. Advantageously, the sensors may be wholly implanted at a tissue site and may be used to take repeated measurements of dissolved oxygen levels at the tissue site without the need for repeated invasive measurement procedures. Specifically, the sensors may be configured to be utilized with standard MR-based spectroscopy. As used herein, the terms "MR-based spectroscopy" and "MR-based methods" broadly refer to analytical and measurement techniques in which a material, such as a material present at a tissue site, is subjected to electromagnetic radiation for purposes of characterization. In particular, the term encompasses analytical techniques in which a magnetic field is applied to a material and the effect of the applied magnetic field on the material is measured or observed such as H1 NMR (hydrogen-1 nuclear magnetic resonance), Flourine-19 NMR, and MRI (magnetic resonance imaging). Although not limited to H1 NMR based techniques, this is a convenient approach because of the ready access to equipment, appropriate pulse sequences, and software.

One embodiment of an implantable sensor 10 is illustrated in FIG. 1. The implantable sensor 10 may include a container 14 having a reservoir 30 that contains a sensing medium. The container 14 may include a mouth portion 22 and a base portion 28. The container 14 may further include a reservoir opening 24 within the mouth portion 22 above the reservoir 30. An oxygen-permeable membrane 16 may be in register with the reservoir opening 24 so as to allow oxygen to diffuse through the membrane 16 and the reservoir opening 24. For example, the membrane 16 may be attached to the container 14 across the reservoir opening 24. The implantable sensor 10 may further include a cap 12 that may be attached to the mouth portion 22 of the container 28 to secure the membrane 16 to the implantable sensor 10 in a position over the reservoir 30. The cap 12 may include a cap opening 18 that is completely or at least partially aligned with the reservoir opening 24 of the container 14 when the cap 12 is secured to the container 14. The cap opening 18 need not occupy the entire width of the cap but may be adjusted to a size sufficient to allow chemical diffusion of oxygen into and out of the reservoir. Alternatively, there may be a plurality of smaller openings on the cap to insure mechanical stability of the device.

The mouth portion 22 of the container 14 may include an external flange 26 which engages a partial internal flange 20 of the cap 12 when the cap 12 is pressed over the mouth portion 22 of the container 14, thereby securing the cap 12 to the container 14 and securing the membrane 16 in place over the reservoir 30. Alternatively, other fastening features may be used for attaching the cap 12 to the container 14, e.g., male and female threading, tabs, snap fingers, quarter-turn fastening structures and the like. In other embodiments, the membrane 16 may be secured over the reservoir 30 with an adhesive. It is possible that the oxygen permeable membrane 16 may be replaced entirely by a fully solid cap which is thin enough to allow permeability of oxygen into and out of the reservoir. In one embodiment, for example, the cap could achieve the necessary thin cross section by having one or a plurality of blind holes or dimples in its surface.

Figure 2:
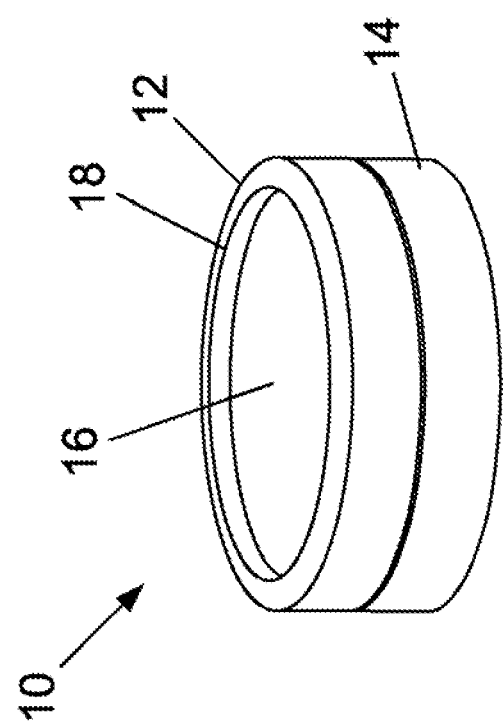
FIG. 2 is a perspective view, illustrating the embodiment of FIG. 1 in an assembled state.

The implantable sensor 10 of FIG. 1 is shown in an assembled state in FIG. 2. When assembled, the implantable sensor 10 may assume a low-profile shape suitable for wholly deploying at a tissue site of a patient. The oxygen-permeable membrane 16 is exposed to fluids at the tissue site via the cap opening 18 of the cap 12. As such, oxygen dissolved in the biological fluid at the tissue site may pass through the oxygen-permeable membrane 16 into the sensing medium.

Although the implantable sensor 10 is shown as being substantially cylindrical in shape in FIGS. 1 and 2, the implantable sensor 10 may be formed into many different shapes. Advantageously, the implantable sensor 10 may be shaped and dimensioned for minimally invasive implantation, for example through a needle or trocar. In some embodiments, the implantable sensor 10 may have a diameter, or width in the plane of the membrane 16, of about 10 mm or less, or more preferably about 1 mm to about 5 mm. In certain embodiments, the implantable sensor 10 may have a diameter less than about 1 mm in diameter. In some embodiments, the implantable sensor 10 may have a depth, measured in a direction substantially perpendicular to the plane of the membrane 16 of about 0.5 mm to about 3 mm, or more preferably about 0.5 mm to about 1 mm. In certain embodiments, the implantable sensor 10 may have a depth less than about 0.5 mm. Other convenient dimensions are those compatible with biopsy tools such as a needle biopsy device.

The container 14 and the cap 12 can be made of various biocompatible materials. The container 14 and the cap 12 may comprise the same material or they may comprise different materials. Preferably, the container 14 and the cap 12 comprise a biocompatible polymeric material, such as a polyethylene polymeric blend, that does not interfere with the detection of dissolved oxygen in the sensing medium. In some embodiments, the container 14 and/or the cap 12 comprise a material that contrasts with the surrounding tissue when subjected to MR-based spectroscopy.

In some embodiments, the sensor 10 comprises a sensing medium in the reservoir 30 that comprises an MR contrast agent for oxygen. The term "MR contrast agent for oxygen" as used herein refers to material suitable for indicating the dissolved oxygen concentration within the material when employing MR-based spectroscopy by enhancing the desired signal beyond that which is provided by background molecules (i.e., molecules naturally present at the site of implantation), such as water molecules. For example, the MR contrast agent for oxygen may comprise a material having a spin-lattice relaxation time (T1) that is dependent on dissolved oxygen concentration. In certain embodiments, the sensing medium may exhibit sufficient sensitivity to resolve oxygen concentration at low oxygen concentrations, particularly between about 0% and 2% oxygen. These sensing mediums include certain liquid or solid compounds having MR properties that are sensitive to oxygen concentration. Particulate suspensions or emulsions of such materials are contemplated.

Proton spins can be flipped into different planes and axis of rotation when protons are irradiated with a radio frequency (RF) pulse. This change in rotation is temporary and the direction in magnetic moment eventually returns to the original configuration. In particular, the restoration of magnetic moments to the original axis can be characterized by T1. As T1 is a material property, it can provide a reliable source of contrast in MRI images; T1 maps are frequently used in imaging applications to distinguish between different anatomical structures. Paramagnetic molecules or particulates that decrease the relaxation time of surrounding molecules can be used to enhance contrast of T1 maps. They can also provide a mechanism for sensing. For example, dissolved oxygen molecules are paramagnetic and can decrease the T1 relaxation time of water protons (or other spin bearing atoms) surrounding it. Thus, the T1 value of these mixtures would depend on the concentration of dissolved oxygen and thus dissolved oxygen concentration can be determined by averaging the T1 of the area.

Figure 3:
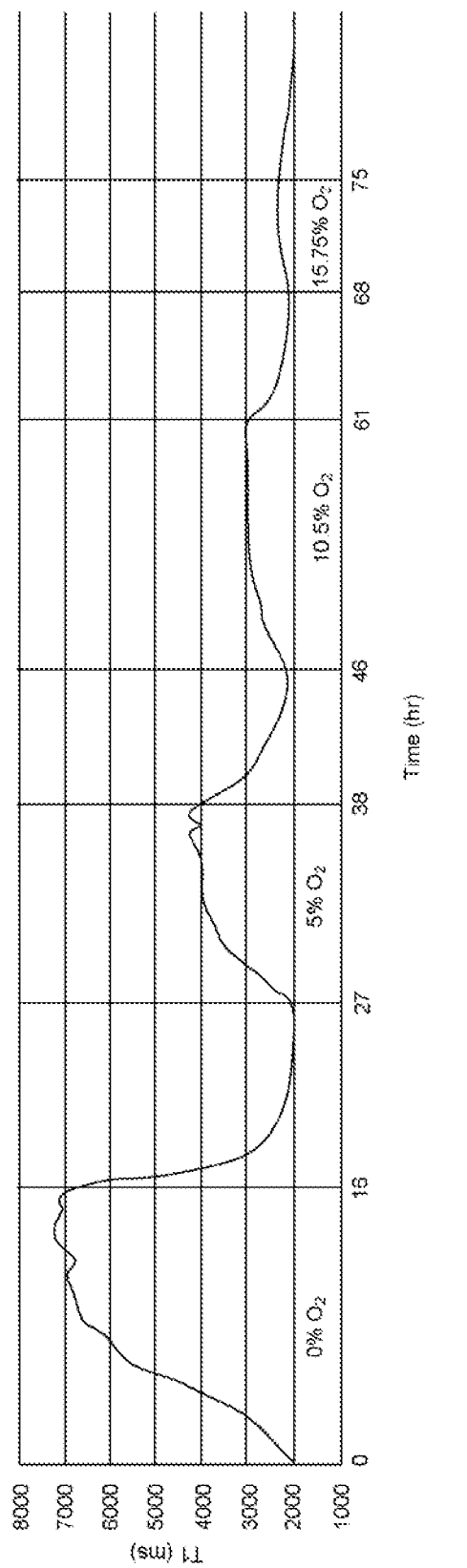
FIG. 3 is a chart, illustrating spin lattice relaxation time (T1) as a function of oxygen concentration for HMDSO.

Instead of using water protons, other materials can also be read using MR-based spectroscopy (e.g., H1 NMR, F119 NMR, or MRI) and some of these materials are more sensitive to concentrations of dissolved oxygen. Indeed, using materials other than water has the advantage that the sensing medium can give a different MR signature and can be more easily distinguished from the background water molecules inside the body. Siloxanes may be particularly useful in sensors as MR contrast agents for oxygen. One particularly useful siloxane is hexamethyldisiloxane (HMDSO), which is a highly hydrophobic and non-polar molecule. This molecule has a high solubility for oxygen, and has a single peak for hydrogen NMR. FIG. 3 illustrates the dissolved oxygen dependent T1 relaxation of HMDSO as measured with a Bruker Minispec. Other potentially useful siloxanes include octamethyltrisiloxane, decamethyltetrasiloxane, dodecamethylpentasiloxane, hexamethylcyclotrisiloxane, octamethylcyclotetrasilane, decamethylgclopentasiloxane, dodecamethylcyclohexasiloxane, and PDMS.

Figure 4:
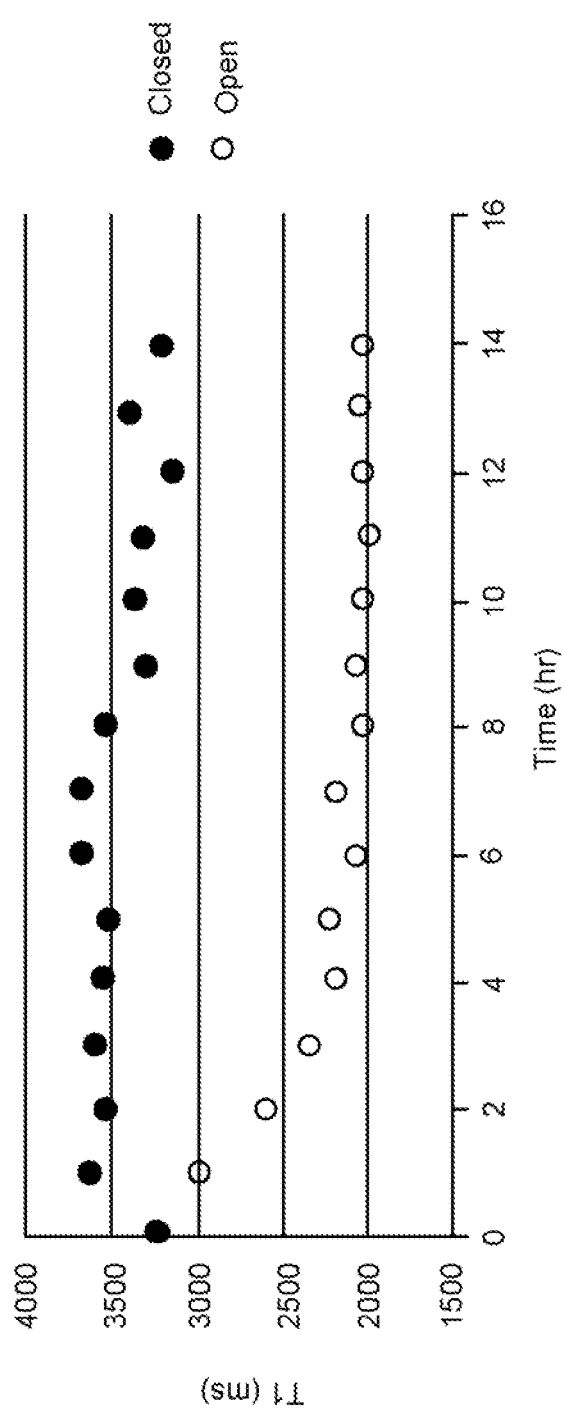
FIG. 4 is a chart, illustrating a sensor's response to an oxygenated environment over time.

FIG. 4 illustrates magnetic relaxation properties of HMDSO loaded in an implantable sensor. The T1 measurements were taken using a single sided magnet (a modified version of an NMRMouse™). The data demonstrates that the sensor is capable of distinguishing between different concentrations of dissolved oxygen in a surrounding environment of aqueous solution. In these measurements, T1 of devices are measured before and after complete deoxygenation of the surrounding environments, and can be seen to reflect increasing levels of oxygen in the surrounding medium. FIG. 4 illustrates the sensor's response to changes in oxygenation conditions. The "closed" data series represent a device that has been left in the deoxygenated environment, whereas the "open" data series represent a device that has been exposed to atmospheric air after the first data point. The sensors may be fully reversible, which would allow for repeated sampling of the same area with changing oxygen content over time.

Other potentially useful materials that may be employed in sensors as a sensing medium include, but are not limited to, compounds that have a high oxygen solubility. For example, perfluorocarbons, a class of highly fluorinated and inert organic compounds, may be used in place of siloxanes as oxygen sensitive agents for use in Fluorine-19 MR systems. Exemplary perfluorocarbons include perfluoro-15-crown-5-ether, hexafluorobenzene, and perfluorotributylamine.

In another embodiment, the implantable sensor may be in the form of a solid polymeric article that has an MR contrast agent for oxygen integrated with the polymeric structure of the article, e.g., by the direct incorporation of MR-readable, oxygen sensitive materials into a polymeric matrix. In a certain embodiment, the implantable sensor may be a cured composite article comprising an MR contrast agent for oxygen dispersed throughout a polymeric matrix. The polymeric matrix material may be permeable to oxygen and may be configured to prevent the diffusion of MR contrast agent for oxygen from the structure at least over the period the sensor device is deployed in vivo, e.g., 1 to 6 months. An exemplary polymeric matrix material is polydimethylsiloxane ("PDMS"). Other polymers that can serve as the matrix material include various UV-curable epoxies and silicones.

Figure 6:
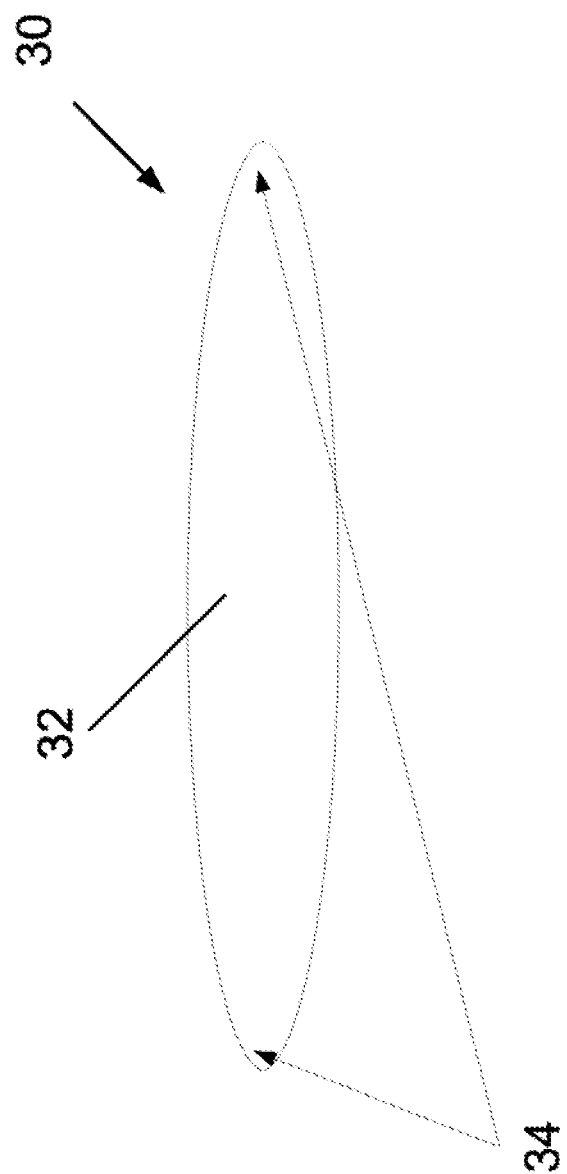
FIG. 6 is a perspective view, illustrating a sensor having a composite polymeric body.

An exemplary polymeric composite sensor 30 is illustrated in FIG. 6. The sensor 30 is formed of a cured polymeric body 32 that may be substantially uniform in composition throughout the body 32. The cured polymeric body 32 may be in the form of a polymeric matrix having an MR contrast agent for oxygen dispersed throughout the body 32. In some embodiments, the MR contrast agent for oxygen is dispersed substantially uniformly throughout the body 32. The MR contrast agent for oxygen may be, for example, a siloxane such as HDMSO or dodecamethylpentasiloxane (DDMPS). In the present example, the body 32 includes corner or portions 34, which may be used as attachment points for securing the sensor 32 to a specific tissue site or otherwise facilitate the embedding of the sensor 32 at the specific tissue site. The body 32 may be formed in any regular or irregular shape as desired.

To fabricate such sensors, an MR contrast agent for oxygen, such as a siloxane, may be added to an uncured liquid polymer base, such as SYLGARD® 184 elastomer base from Dow Corning, and mixed thoroughly. An appropriate curing agent may then may be added, and the mixture/solution may be cured, e.g., with heat treatment, to form a solid composite article. These solid composite articles may be directly used in oxygen sensing applications without further modification or can be coated with other materials to enhance biocompatibility, stability, and/or containment of the MR contrast agent for oxygen. For example, the polymeric body may further include PDMS or another oxygen permeable material that is completely or substantially impermeable to the MR contrast agent for oxygen.

Polymeric composite sensors may be made in various shapes and sizes. In certain embodiments, the sensor is about 1 mm or more in size. Such a size is suitable for imaging based on the resolution of most clinical scans. The shape of devices may be negative impressions of the mold forms in which they are cured. The mold forms and sensor shapes can be designed in shapes that facilitate implantation. They can also be designed to impact particular features on molded devices, such as anchor points for attaching the device to implantation site.

In another embodiment, the implantable sensor may be in the form of a beads or microspheres. For example, in one embodiment, the sensor is composed of a single or a plurality of fine beads or microspheres each containing an agent whose MR relaxivity is sensitive to oxygen. The beads or microspheres may consist of a core of the MR contrast agent encapsulated by the oxygen permeable material. The beads may be spherical or non-spherical (e.g., elongated, like grains of rice). One advantage of such an embodiment is that the sensor(s) may be injected through a conventional hypodermic needle/syringe into one or more tissue sites in the patient, providing a minimally invasive route to deploy the sensor into the patient's body. In some embodiments, the beads or microspheres may have a volume average diameter of about 100 microns or less. In certain embodiments, the beads or microsperes may have a volume average diameter of about 20 microns or less. The beads or microsperes may be provided in an injectable formulation, for example, as a colloidal or other suspension with pharmaceutically acceptable liquid known in the art.

In one example, each bead is composed of a shell that has a primary purpose of providing mechanical stability and permeability to oxygen and an interior volume in which the MR sensitive material resides. The shell and interior volume materials may be very similar to one another in their chemistry, but they may differ in their mechanical properties. The interior may, for example, be a low molecular weight or liquid silicone derived material but the shell may be a high molecular weight or cross linked silicone material in such a way that it provides sufficient strength to the bead. In another example, the core and the shell are comprised of the same material and substantially indistinguishable.

Figure 7:
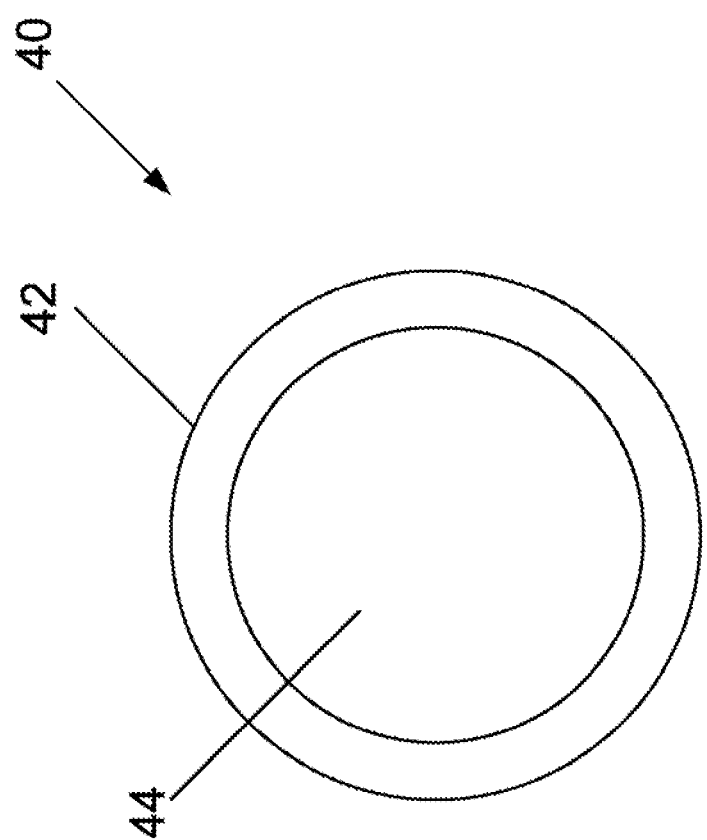
FIG. 7 is a section view, illustrating one embodiment of a sensor in a bead form.

An exemplary embodiment of a bead sensor 40 is illustrated in FIG. 7. The sensor 40 includes an oxygen permeable shell 42 that surrounds a sensing medium core 44. The sensing medium core 44 more comprise an MR contrast agent for oxygen, such as a siloxane.

In another embodiment, the beads may be in the form of composite polymeric particles comprising an MR contrast agent for oxygen dispersed throughout a polymeric matrix. For example, the particles may comprise a PDMS matrix and a siloxane, such as DDMPS or HMDSO, dispersed throughout the polymeric matrix. In some embodiments, no shell is provided around the composite polymeric particles. In other embodiments, an oxygen-permeable shell material may be provided around each of the beads for improved biocompatibility or stability.

The beads may be formulated into an injectable suspension using one or more liquid vehicles or pharmaceutically-acceptable excipients known in the art. In a particular embodiment, it may be advantageous to incorporate a gel in the formulation of such beads so that they remain in one location within the body after injection, e.g., proximate to the injection site. Suitable gels and gelling materials for parenteral use are known in the art. The volume of the formulation (and beads) administered in a given injection is adjustable. Thus, one may insure that the total volume of oxygen sensitive material is sufficient to image in any given MRI instrument.

The sensor may be packaged for shipping and storage. It may be sterilized before or after packaging. For example, sterilization may be achieved by ionizing radiation (gamma or electron beam) or ethylene oxide (EtO) as known in the art. In one embodiment, the container is made from a gamma-irradiation stable, biocompatible polymer known in the art.

Methods of Use

In another aspect, a method is provided for measuring the dissolved oxygen concentration of the extracellular environment in vivo. The method may include deploying a sensor at a tissue site, and thereafter subjecting the tissue site to electromagnetic radiation and employing MR-based spectroscopy to analyze the dissolved oxygen concentration of the fluid. The sensor may comprise a sensing medium that comprises an MR contrast agent for oxygen contained in a reservoir.

In some embodiments, the implanted device may be used to analyze the dissolved oxygen concentration of a tissue site at the same location(s) over time. Because of the non-invasive nature of the "sampling" analysis, the "sampling" may advantageously be performed more frequently or over a shorter sampling interval. Compared to the injection of HMDSO directly into tissue, the implantable devices may also offer the advantage of confining the molecules to a known space and also keeping the amount of HMDSO sampled constant. In injection methods, it may be difficult to ascertain a specific amount of contrast agent in a specific area; as the contrast agent is cleared from the body, the exact amount of contrast agent remaining can also be difficult to determine. The use of the sensor devices may alleviate these problems, as the molecules are prevented from escaping by the oxygen permeable membrane.

In some embodiments, one or more sensors are implanted in a patient. For example, the sensors may be placed at or adjacent to or within an organ or tissue site of interest in the patient, such as the brain, the heart, or other vital organ. The sensors may also be placed at or around the site of a tumor. The sensors may be subjected to MR-based spectroscopy for analysis or imaging. In some embodiments, the sensors and tissue site may be analyzed by measuring T1 relaxation times using MRI. These measurements may be taken repeatedly, such as over the course of a patient's treatment for a disease.

In some embodiments, one or more sensors are used to monitor hypoxia within solid tumors. The one or more sensors may be implanted in or around the tumor tissue. For example, the one or more sensors may be implanted during a resection surgery or a biopsy procedure. Thereafter, the tumor site may be analyzed or imaged using MR-based spectroscopy, such as H1 NMR or MRI. The measurements may be repeated regularly and non-invasively as needed. A physician or other health care professional may use the dissolved oxygen data obtained from the sensors to manage the treatment of the patient. For example, the physician or health care professional may used the dissolved oxygen data from the sensor to evaluate the state of the tumor, to identify hypoxia conditions in tumors, to evaluate the effectiveness of a treatment strategy on the patient, and to schedule therapies, such as radiotherapy, at the most opportune times to achieve improved outcomes.

Other applications for measurement of dissolved oxygen include the monitoring of metabolic activities in specific regions or organs of the body. One highly investigated area is the use of MRI techniques to probe oxygen usage in the brain in functional MRI studies. Biologists studying neural activities can glean information on the functions of those areas by monitoring the usage of oxygen in different regions of the brain. Oxygen depletion in parts of the body can be detected with implanted sensors, specifically, detecting oxygen depletion in vital organs such as the heart or brain can potentially inform physicians of problems (e.g., minor myocardial infarction or stroke) that can otherwise go unnoticed.

Another application is the staging of compartment syndrome in trauma patients and whether a fasciotomy is indicated. The swelling that occurs in an injured limb of a trauma patient can dramatically reduce blood flow to the limb which can ultimately lead to necrosis of the tissue. A surgical procedure where the fascia is cut to reduce such pressure (a fasciotomy) is called for when there is insufficient circulation in the limb. One indicator of that circulation is interstitial dissolved oxygen. An oxygen sensitive device placed in the limb and monitored over time will be very helpful in quantitative assessment of the level of compartment circulation.

These sensor devices may be used in other clinical and research applications. The sensor devices may provide physicians and researchers unprecedented access to real-time $pO_2$ data without affecting patients' quality of life.

These sensor devices may also be employed in ex vivo applications. For example, the sensors may be used in ex vivo applications in which it is desirable to determine the oxygen concentration of a fluid, such as a liquid or a gas. In some embodiments, an electromagnet, such as an electromagnet comprising a coil and a rare-earth magnet, may be used to measure the relaxivity of a sensing medium when it is in contact with the fluid. The sensing medium may be an MR contrast agent for oxygen. As the oxygen content of the fluid changes, the relaxivity of the sensor medium will also change, and the change in the relaxivity of the sensing material may be detected by a sensing circuit that is electrically connected to the electromagnet. The sensing circuit may be calibrated to detect changes in the relaxivity of the sensor material that are of significance, to the particular sensing application. For example, in sensing application in which a 1% change in oxygen concentration from a set point of 10 volume percent oxygen concentration would be of significance, the sensor may be calibrated by employing the appropriate amount of sensing medium with an appropriately-sized electromagnet and an appropriately-calibrated sensing circuit to detect changes of the magnitude of concern in the sensing application. Of course, the foregoing percentages are only intended to be illustrative, and one of ordinary skill in the art will appreciate that, consistent with the present disclosure, the actual control set points and degree of change in concentration that is of significance may vary depending on the particular application and the disclosed sensors and methods may be calibrated to the particular application.

In a certain embodiment, the sensor may be employed in an automobile to determine oxygen concentration in an exhaust stream. For example, a sensor may be placed in the exhaust stream flow path, such as downstream and/or upstream of a catalytic converter in a location in the exhaust stream flow path that exposes the sensing medium to the exhaust stream. The sensing medium may be positioned and arranged with respect to an electromagnet such that changes in the relaxivity of the sensing medium may be detected by a sensing circuit that is electrically coupled to the electromagnet. The sensing circuit may detect the oxygen concentration of the exhaust gas at the location of the sensor. The oxygen concentration may be an absolute oxygen concentration or it may be change in concentration from a pre-designated control set point. The sensor may communicate with a controller, e.g., via an electrical connection between the sensor and controller or via telemetry. The controller may then control an actuation function when the measured oxygen concentration meets, exceeds, or is less than a set point. For example, the controller may control the actuation of a change in fuel injection, e.g., by injector pulse-width modulation or by altering pulse frequency, to achieve a desired air-fuel ratio, such a stoichiometric air-fuel ratio.

In addition to automotive sensing applications, other ex vivo applications are envisioned for the present sensors. For example, the sensors may be used to measure dissolved oxygen in bodies of water such as lakes, rivers, and oceans. In such applications, the sensing medium may be submerged into the body of water, and a sensing circuit that is coupled to an electromagnet may detect changes in relaxivity of the sensing medium as the concentration of dissolved oxygen around the sensor changes.

EXAMPLE

Three composite sensors having different concentrations of contrast agent in a matrix material were produced. Each sensor was produced by adding dodecamethylpentasiloxane (DDMPS) to SYLGARD® 184 elastomer base from Dow Corning. The liquid mixture was then mixing thoroughly, poured into a mold, and then cured to produce solid composite sensors. The three samples were 75% DDMPS, 50% DDMPS, and 25% DDMPS (percentages expressed in volume percent).

Figure 5:
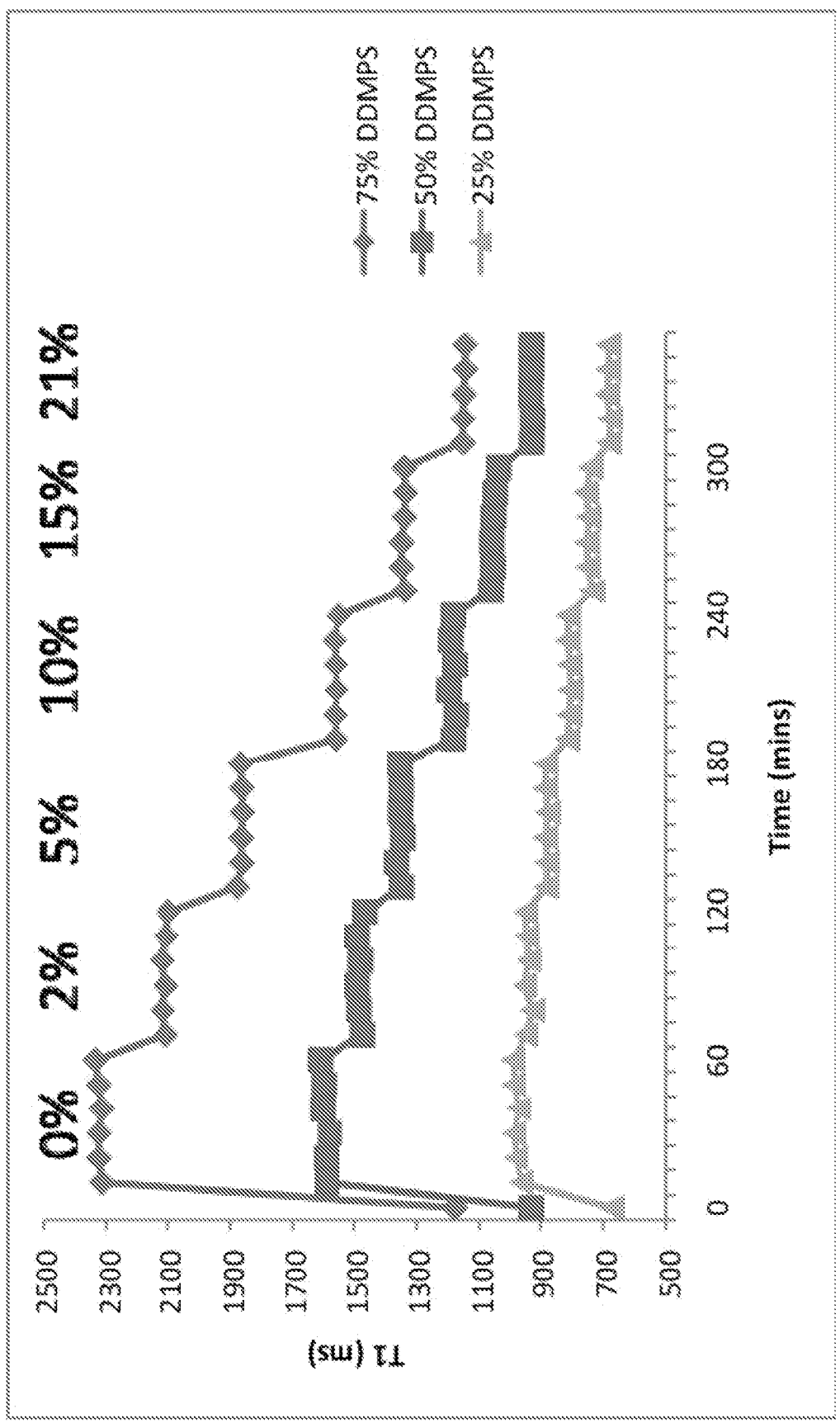
FIG. 5 is a chart, illustrating spin lattice relaxation time (T1) as a function of oxygen concentration in a sensor comprising a DDMPS/PDMS composite body.

Spin-lattice relaxation time (T1) data has been collected for each device. Each of the three molded PDMS/siloxane devices were placed in a 10 mm NMR tube and then inserted into a Bruker Minispec TD-NMR system for measurements. Gas composition in the tube was altered with the use of a gas mixer that outputs gas mixtures at different oxygen concentrations. The T1 data for three samples is illustrated in FIG. 5. The numbers at the top of the graph indicate the oxygen concentration around the sample when measurements were taken. As shown in FIG. 5, the measured T1 for each sample correlate strongly with oxygen concentration and therefore provide a good indicator for dissolved oxygen concentration.

While the present invention may be embodied in many different forms, disclosed herein are specific illustrative embodiments thereof that exemplify the principles of the invention. It should be emphasized that the present invention is not limited to the specific embodiments illustrated.

We claim:

1. A sensor for measuring a dissolved oxygen concentration in vivo when implanted at a tissue site, comprising:
    a solid implantable article having a sensing medium contained therein, the sensing medium comprising a magnetic resonance (MR) contrast agent for oxygen that has a spin-lattice relaxation time that is dependent on dissolved oxygen concentration;
    wherein the solid implantable article is a solid oxygen-permeable polymeric siloxane matrix configured to prevent diffusion of the MR contrast agent from the implantable article while the sensor is implanted at the tissue site,
    wherein the MR contrast agent is uniformly dispersed throughout the matrix and retained within the matrix, wherein the MR contrast agent comprises a siloxane or a perfluorocarbon, and wherein the MR contrast agent siloxane and the matrix siloxane are different types of siloxane, and
    wherein the sensor is configured to indicate the dissolved oxygen concentration in vivo at the tissue site when subjected to an MR-based method.

2. The sensor of claim 1, wherein the matrix comprises polydimethylsiloxane (PDMS).

3. The sensor of claim 1, wherein the sensor is in the form of a bead.

4. The sensor of claim 1, wherein the implantable article comprises a material that contrasts with the tissue site when subjected to MR-based spectroscopy.

5. The sensor of claim 1, wherein the MR contrast agent is a siloxane.

6. The sensor of claim 5, wherein the polymeric siloxane matrix is polydimethylsiloxane, and wherein the MR contrast agent comprises hexamethyldisiloxane, octamethyltrisiloxane, decamethyltetrasiloxane, dodecamethylpentasiloxane, hexamethylcyclotrisiloxane, octamethylcyclotetrasilane, decamethylgclopentasiloxane, dodecamethylcyclohexasiloxane, or a combination thereof.

7. The sensor of claim 1, wherein the implantable article is 1 mm or more in size.

8. A sensor for measuring a dissolved oxygen concentration in vivo when implanted at a tissue site, comprising:
    a solid implantable article which comprises
        a magnetic resonance (MR) contrast agent for oxygen that has a spin-lattice relaxation time that is dependent on dissolved oxygen concentration, the MR contrast agent comprising a siloxane or a perfluorocarbon; and
        a solid oxygen-permeable polymeric siloxane matrix,
        wherein the MR contrast agent is dispersed uniformly throughout and retained within the polymeric siloxane matrix, preventing diffusion of the MR contrast agent from the implantable article while the sensor is implanted at the tissue site, and
        wherein the solid implantable article is 1 mm or more in size and configured to indicate the dissolved oxygen concentration in vivo at the tissue site when subjected to a MR-based method.

9. A sensor for measuring a dissolved oxygen concentration in vivo when implanted at a tissue site, comprising:
    a solid implantable article having a sensing medium contained therein, the sensing medium comprising a magnetic resonance (MR) contrast agent for oxygen that has a spin-lattice relaxation time that is dependent on dissolved oxygen concentration;
    wherein the implantable article is an oxygen-permeable polymeric siloxane matrix configured to prevent diffusion of the MR contrast agent from the implantable article while the sensor is implanted at the tissue site,
    wherein the MR contrast agent is dispersed throughout the matrix and retained within the matrix, wherein the MR contrast agent comprises a siloxane or a perfluorocarbon, and wherein the MR contrast agent siloxane and the matrix siloxane are different types of siloxane, and
    wherein the sensor is configured to (i) indicate the dissolved oxygen concentration in vivo at the tissue site when subjected to an MR-based methoda, and (ii) prevent diffusion of the MR contrast agent from the implantable article for a period of 1 to 6 months.

* * * * *